United States Patent [19]

Frye et al.

[11] Patent Number: 5,699,908
[45] Date of Patent: Dec. 23, 1997

[54] SCALPEL BLADE REMOVAL AND STORAGE APPARATUS

[75] Inventors: Lloyd H. Frye, Baton Rouge, La.; Clarence Zierhut, Garland, Tex.

[73] Assignee: Fryco, Inc., Baton Rouge, La.

[21] Appl. No.: 638,978

[22] Filed: Apr. 25, 1996

[51] Int. Cl.$^6$ .................................................. B65D 83/10
[52] U.S. Cl. ........................ 206/355; 29/239; 30/339
[58] Field of Search ........................... 206/355, 359, 206/349, 363; 30/339; 29/239

[56] References Cited

U.S. PATENT DOCUMENTS

| | | |
|---|---|---|
| 3,172,316 | 3/1965 | Grieshaber . |
| 4,168,777 | 9/1979 | Gaskell et al. . |
| 4,270,416 | 6/1981 | Thompson . |
| 4,378,624 | 4/1983 | Klingenberg . |
| 4,386,457 | 6/1983 | Coombs ............................ 206/355 |
| 4,395,807 | 8/1983 | Eldridge, Jr. et al. . |
| 4,466,539 | 8/1984 | Frauenhoffer ...................... 29/239 |
| 4,730,376 | 3/1988 | Yamada . |
| 4,746,016 | 5/1988 | Pollak et al. . |
| 4,903,390 | 2/1990 | Vidal et al. ........................ 206/359 |
| 4,998,334 | 3/1991 | Pemberton et al. . |
| 5,088,173 | 2/1992 | Kromer et al. . |
| 5,406,684 | 4/1995 | Carson . |

*Primary Examiner*—Paul T. Sewell
*Assistant Examiner*—Nhan T. Lam
*Attorney, Agent, or Firm*—Pravel, Hewitt, Kimball & Krieger

[57] ABSTRACT

A scalpel blade removal apparatus for use with common surgical handle having a slotted tang and a disposable or changeable blade. The apparatus includes a receptacle for holding a multiple blades that have been disposed of. A cam arrangement is operated by the tang as the surgeon pushes the handle into the receptacle. The upper end of the cam rotates, disengaging the proximal end of the blade from the tang and simultaneously forming a connection between the proximal end of the blade and a shoulder that defines a catch. When the cam rotates fully to its lower most position, the blade is fully disengaged. The surgeon then removes the handle by pulling the handle along the same path used to insert the handle and blade. The catch then retains the blade so that only the handle and its tang are withdrawn.

10 Claims, 4 Drawing Sheets

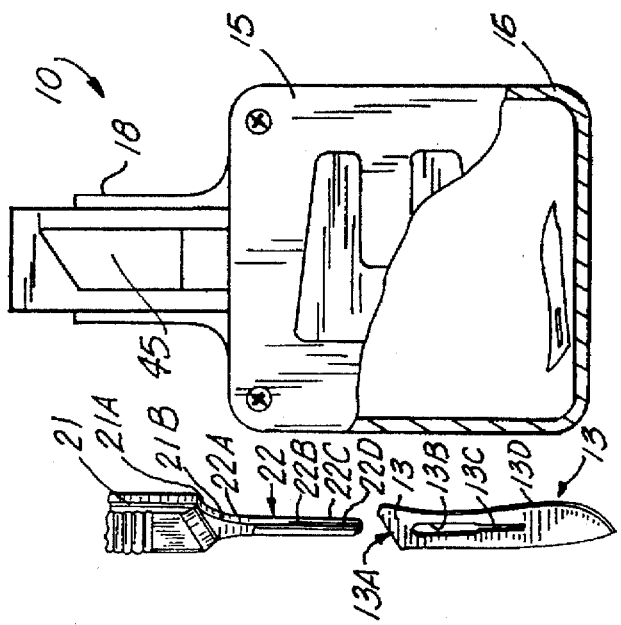
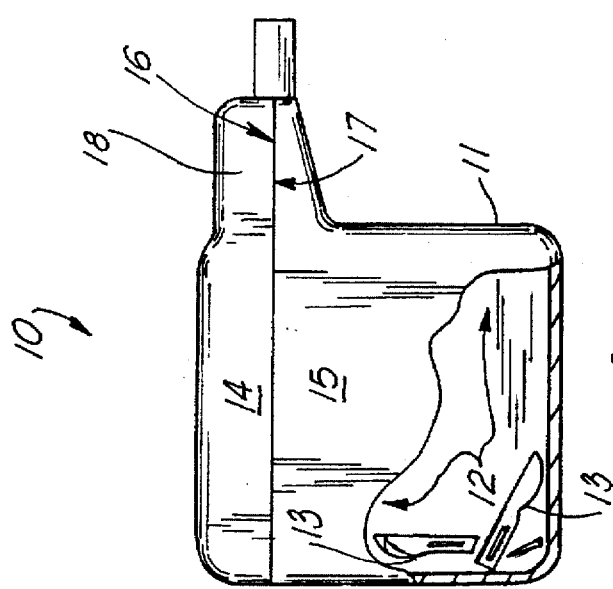
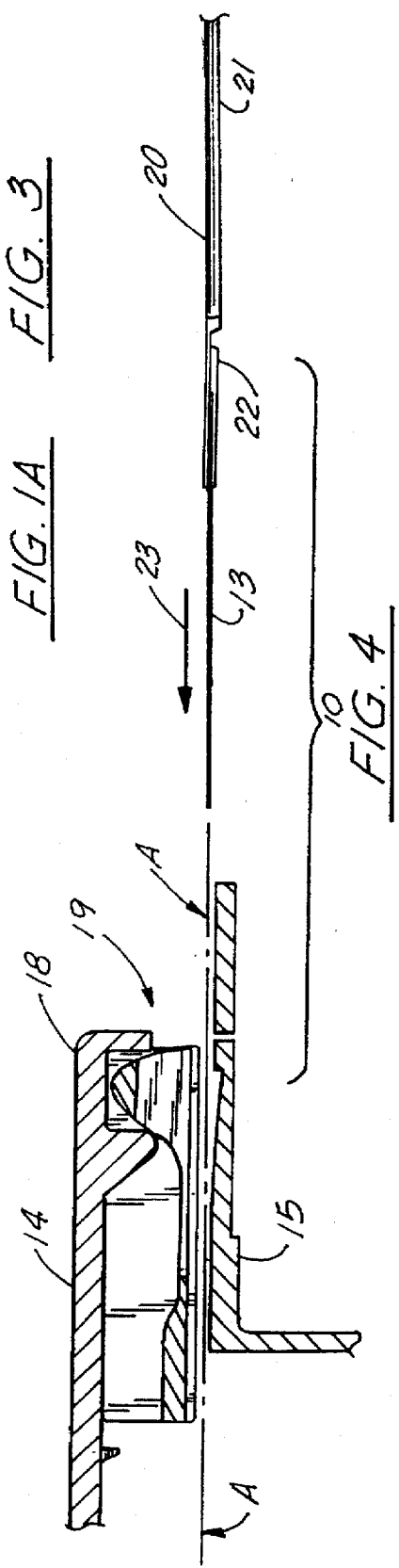

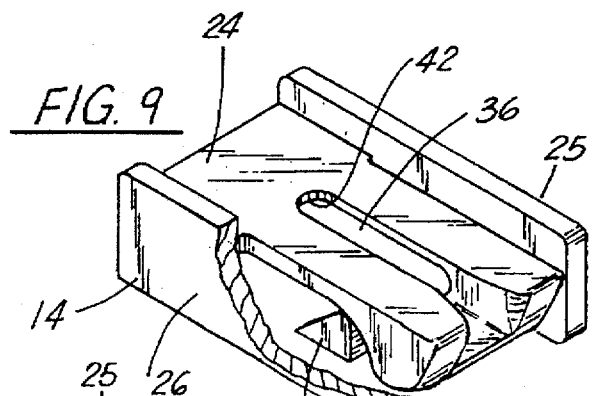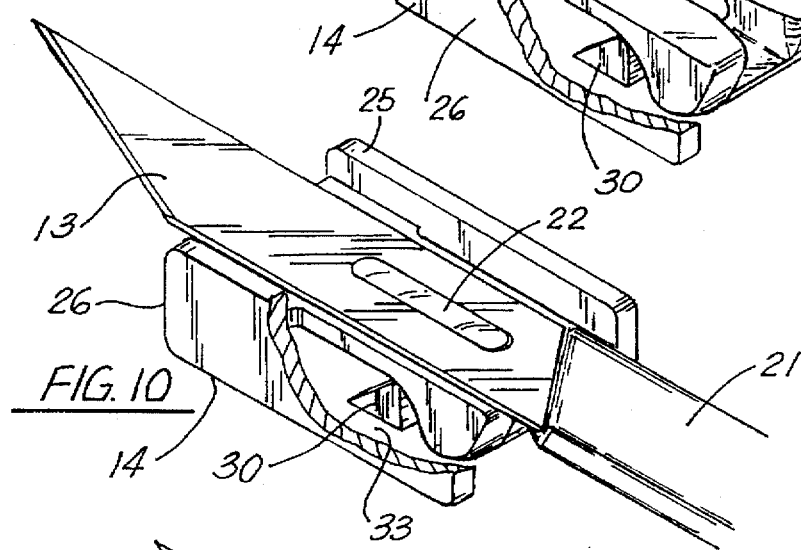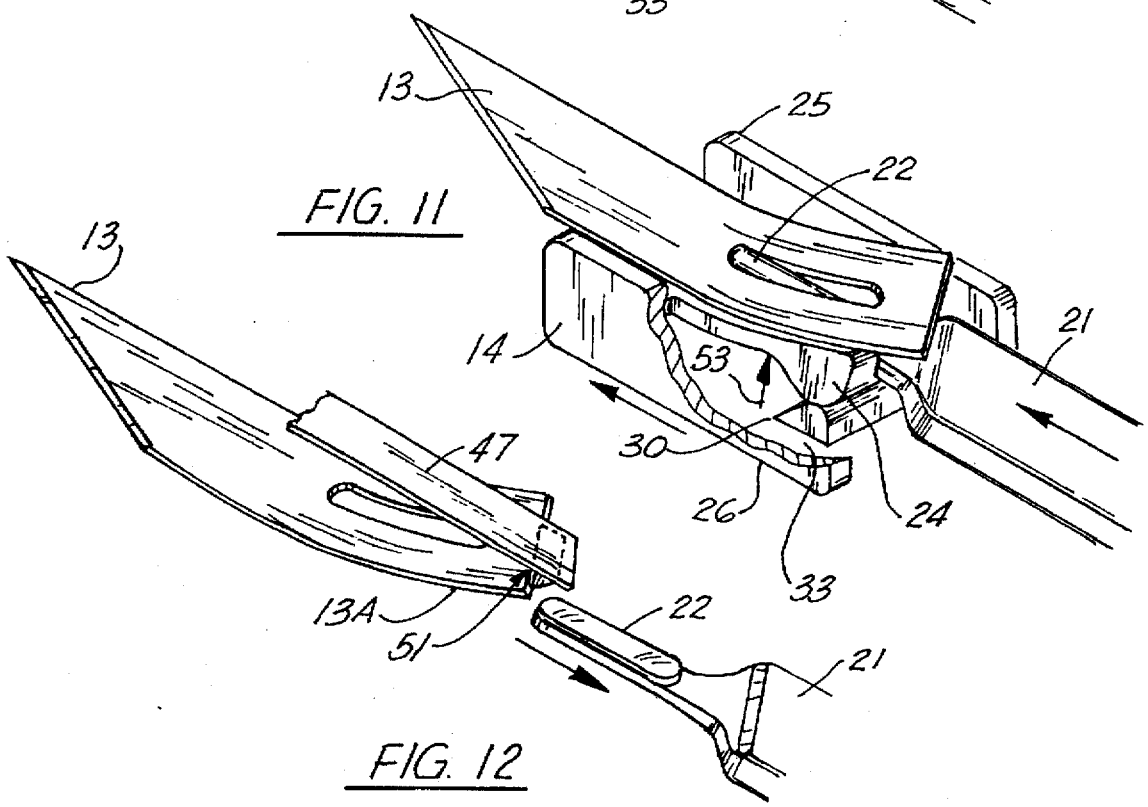

SCALPEL BLADE REMOVAL AND STORAGE APPARATUS

BACKGROUND OF THE INVENTION

1. Field of the Invention

The removal of surgical scalpel blades from a scalpel handle and more particularly relates to an improved surgical blade remover that allows the user to safely and efficiently remove the disposable surgical blade of a scalpel from the reusable handle portion wherein the user moves the blade and its handle along a linear path into a receptacle that bends and then engages the blade, a moving cam dislocating the proximal end of the disposable scalpel blade from the handle as the blade bends so that when the user withdraws the handle the blade is captured within a receptacle and without the necessity of the user involving a second hand, thus eliminating risk of cutting or infection.

2. General Background

A surgical scalpel typically comprise an elongated handle having a distal end portion with a tang having channels or grooves that receive a scalpel blade. The scalpel blade that is commonly used throughout hospitals and physician's offices has a two part slot including a thicker portion and a thinner portion though those two portions are continuous. This common scalpel apparatus affords that surgeon with a rugged structurally sound cutting knife for use in surgical procedures. However, removal of the blade from the handle is dangerous to the surgeon or nurse as the risk of cutting and infection and/or contamination is always present.

Devices are known in the art for removing blades from scalpel handles. An example of such a patent is the Grieshaber U.S. Pat. No. 3,172,316 entitled "Blade-Removing Tool". FIG. 5 of the '316 illustrates a typical blade and handle and changeable/disposable blade arrangement that is still used today in the medical industry. The Grieshaber '316 is incorporated herein by reference.

A scalpel blade extractor is disclosed in U.S. Pat. No. No. 4,270,416. In the U.S. Pat. No. 4,270,416 there is provided a hand held device which permits safe removal of used blades from scalpels or the like in which a slotted blade is received in opposed lateral grooves of a thin elongated tang. A proximal region of the blade is located behind the tang in a cut-away, laterally convergent region intermediate the tang and the handle. The device includes a base wall over whose surface the scalpel is advanced and having laterally opposed protuberant regions over which the blade slides. A slot between the protuberant regions receives the tang but not the blade. A fully inserted position of the scalpel is defined by abutment between the proximal edges of the protuberant regions and the convergent region. A rear wall is supported behind the slot with its lower edge spaced from the base wall to allow the scalpel and blade to be inserted therebetween and to allow a fully inserted scalpel to be pivoted about the lower edge to a tilted orientation in which the proximal end of the blade is levered away from the intermediate region clear of the tang and is retained by interference with the rear wall during removal of the scalpel handle in the tilted orientation. Guide surfaces proximally of the slot direct the scalpel blade or handle into the slot.

The Klingenberg U.S. Pat. No. 4,378,624 discloses a scalpel blade remover in which the blade is clamped against a fixed block by manipulating a lever to cause a movable block to move toward the fixed block. The movable block is preferably made of resilient material and all other elements of the structure are made of metal such as stainless steel, the components being autoclavable. A tab is provided on the movable block to engage an end of the blade and move that end relative to the body of the blade and the scalpel handle to disengage the blade from the handle. The blocks are mounted upon a supporting surface, beneath which a sterile disposable box may be disposed. The supporting surface is slotted in a plane which includes the area of clamping of the scalpel blade between the fixed and movable blocks. The movable block may also be provided with a guide portion to ensure the clamping action, and the movable block may be provided with a relieved or cut-off end permitting a scalpel blade to be disengaged from the scalpel handle.

A surgical blade remover is disclosed in U.S. Pat. No. 4,395,807 issued to John Eldridge. The '807 discloses such a surgical blade remover wherein a surgical blade is easily and effectively removed from the tang of a handle. The device is provided with two members which are spaced to form a channel sized to permit the tang to be positioned between them while the blade rests on the upper surfaces of the members. The channel between the members at their lower portions widens to permit the-handle to enter the channel sufficiently that the heel of the blade can abut a projection which extends upward from each surface of the members. The handle enters this widened lower portion of the channel while the blade rests against the upper surfaces of the members thereby releasing the heel of the blade from the tang. The blade can then be removed from the handle by pulling the handle out of the channel because the projections prevent the blade from moving with the handle.

The Yamada U.S. Pat. No. 4,730,376 discloses a blade removal apparatus for a changeable blade scalpel which is removably mounted on a scalpel handle by fitting a mounting hole formed in the blade over a blade mounting part having a narrow width provided on the tip end of the scalpel handle. The blade removal apparatus has a box part having an open top and a side wall and an acceptor part projecting laterally from the upper part of the side wall, and a cover part closing the open top and having a visored part extending over the acceptor part. A guide edge on the acceptor part defines a lower gap tapered so as to become narrower as it extends to the inside of the box part and into which blade mounting parts of changeable blade scalpels of various types can be inserted. The cover part has a stopping stepped part defining an upper gap between the lower surface of the visored part and the guide edge and into which upper gap a blade on a scalpel is insertable. The stopping stepped part has an angle notch engageable by a blade root end edge on a blade. A pair of stoppers project from the lower side of the cover part of both sides of the lower gap. A push button can be pushed down from the cover into the box part and, having a pair of projection pieces which make contact with the stoppers for forcing the blade surface located on both sides of the blade mounting part on the scalpel down for lifting the blade root end edge of the blade, and thereby causing the blade root and edge to be engaged with the angle notch of the stopping stepped part.

The Pollack et al. U.S. Pat. No. 4,746,016 discloses a mechanism for mounting and removing a blade having an elongated slot mounting means from a blade handle which has a mounting boss from insertion into the elongated slot. The mechanism includes a handle guide for forming one side of a passageway for insertion of the handle therethrough, the handle guide having a flexible body which is sufficiently flexible to allow deflection of the handle for withdrawal of the boss out of mating relationship with the elongated slot. The mechanism further includes blade extracting means fixed opposite the handle guide forming a second side of the passageway and having a blade retaining projection arranged adjacent the passageway which can be actuated to prevent withdrawal of a blade from the passageway. An actuation means is included which is fixed for actuation of the blade extracting means upon deflection of the handle sufficient to disengage the boss from mating relationship with the elongated slot so that a blade mounted on the handle can be removed therefrom when the handle is withdrawn from the passageway. The apparatus also includes a device including such mechanism in combination with a blade retaining and/or disposal well which can serve as a blade dispenser and/or disposal device.

The Gaskell et al. U.S. Pat. No. 4,168,777 discloses a scalpel blade remover and collector device for removing and storing the blade of a scalpel of the type comprising a handle having a reduced section at one end thereof with an elongated boss on one side of said reduced section, said boss having a recess partially extending along each side thereof, and a blade having an elongated slot therein with a reduced section, said slot being complemental to said recessed boss, such that the blade is retained on said boss when the reduced section of the blade slot engages the recess on the boss, comprises a container adapted to accommodate at least one blade, an aperture in said container shaped to allow the introduction of the blade retaining end of the scalpel into said container, abutment means projecting outwardly from said aperture adapted to abut against the inner end of the blade when the handle is removed from said container restraining the blade from outward movement thereof and allowing retention of the blade in the container.

The Pemberston et al. U.S. Pat. No. 4,998,334 discloses a blade extractor for a replaceable blade instrument or tool, which comprises upper and lower tabs of length slightly exceeding that of a blade to be extracted, and of width slightly exceeding that of a blade to be extracted with side skirts provided on one or both tabs, abutment means provided on one tab, and with the tabs being hinged together and being manually and progressively displaceable from a splayed-apart, open position to a closed position, in which closed position the tabs encapsulate the blade, and lie in substantially parallel planes, with opposite longitudinal edges of the tabs and hence the extractor closed off by the side skirts, and the abutment means engages a portion of the blade so that, when the user maneuvers the instrument or tool with respect to the extractor during the extraction process, the blade is safely encapsulated within the extractor.

In the Kromer U.S. Pat. No. 5,088,173, a remover-receptacle device bends a scalpel blade having a central longitudinal aperture presenting detents from its mounted position on the tang of a scalpel blade handle so as to remove the blade from the handle. In the removal the distal, blade-end region of the scalpel blade is held completely planar from a position proximal of the detents while only the scalpel blade's proximal, shank-end region is bent. The scalpel handle's tang may thusly be slid from the scalpel blade's aperture with essentially zero removal force. The act of removing the scalpel blade locks the scalpel blade remover-receptacle shut with exactly one scalpel blade, visible through a viewing aperture, present therein. Both the one-time-use scalpel blade remover-receptacle and the single removed scalpel blade encapsulated therein are said to be safely transported and disposed.

The Carson U.S. Pat. No. 5,406,684 discloses a sanitary surgical blade removal instrument for removing a disposable blade from the handle of a surgical tool. The instrument consists of a piece of sheet metal bent at a C-shaped flexible fold to produce an upper portion and a lower portion which extend generally parallel to one another. The upper and lower portions of the sheet metal form the upper and lower portions of a blade gripping and flexing end and the upper and lower portions of a handle end. To use the blade removal instrument, the surgical tool is inserted into the removal instrument so that the neck of the surgical tool rests within a lower notch in a lower ridge of the lower portion of the removal instrument such that the lower ridge on either side of the lower notch engages the underneath side of the disposable blade. The user squeezes the upper and lower portions of the handle of the removal instrument, keeping his hand at a safe distance from the sharp contaminated blade. The handle of the surgical tool may then be pulled away from the blade while the blade remains securely gripped in the gripping section of the removal instrument. The blade may then be disposed of safely with the hand of the user safely positioned on the handle of the instrument, away from the contaminated sharp blade. Finally, the removal instrument may be sterilized so the removal instrument may be reused.

SUMMARY OF THE INVENTION

Many of these prior art patents and devices suffer because they require two hands of the user during the critical time that the blade is separated from the handle. This is quite dangerous because of the risk of cutting and/or infection. Further, if the surgeon is wearing surgical gloves, it is very possible that one of the surgeon's gloves can become torn or contaminated during removal of the blade when both hands are necessarily involved.

Another problem of many prior art devices is that they require the actuation of a separate button or activator in order to remove the blade. This is dangerous because it requires the surgeon to apply an unknown amount of pressure in order to separate the knife from the handle. This is especially dangerous in situations where the blade is hidden from the surgeon's view when the surgeon applies pressure in order to hopefully disengage the blade from the handle.

Other types of prior art devices for separating a surgical scalpel blade from its handle require that the user twist or bend the scalpel handle as part of the removal operation. This is awkward and potentially dangerous because the user does not know how far to bend the blade in order to properly disengage the scalpel blade from the handle.

The present invention solves these prior art problems and shortcomings by providing a method and apparatus for removing a scalpel blade from a scalpel handle wherein the user is only required to use one hand. Further, the present invention provides a scalpel blade removing apparatus that requires no bending or twisting of the handle by the user. With the present invention, the user simply pushes the blade and its handle into a receptacle along a linear path until it stops and then pulls the handle back from the blade along the exact same linear path. This produces a very simple in and out travel path for the handle that can be easily tracked by any user. Because the scalpel blade moves along the same path during insertion and removal, very little risk occurs that the surgeon will improperly disengage the blade from the handle or ineffectively disengage the blade from the handle.

The above objects are accomplished by providing a surgical blade removal apparatus that includes a cam member that rotates when linear pressure is applied to the scalpel blade as it is move along a generally linear path. The cam is engaged by the tang of the handle which then pushes the cam down. The cam then rotates at one end portion about a designed point of rotation so that only the proximal end of the blade is bent to deflected, thereby disengaging the proximal end of the blade from the tang.

Once the handle reaches a stop, the surgeon automatically knows that the blade has in fact been disengaged from the handle. Once this stop is reached, the surgeon simply withdraws the blade along the same path. A shoulder within the receptacle grabs the proximal end of the blade when the blade is in the bent or deflected position. The handle and tang can be removed from the receptacle while the blade remains in the receptacle, held by the stop.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is perspective view of the preferred embodiment of the apparatus of the present invention;

FIG. 1A is a fragmentary perspective view of a typical scalpel handle and its changeable blade;

FIG. 2 is a side view of the preferred embodiment of the apparatus of the present invention;

FIG. 3 is a rear view of the preferred embodiment of the apparatus of the present invention;

FIG. 4 is a sectional view illustrating the method and apparatus of the present invention during an insertion of a surgical scalpel handle and its blade into the receptacle portion of the apparatus of the present invention;

FIG. 9 is a partial perspective view of the preferred embodiment of the apparatus of the present invention;

FIG. 10 is a partial perspective view of the preferred embodiment of the apparatus of the present invention illustrating a scalpel being placed in the initial position prior to a camming of the blade away from the handle;

FIG. 11 is a fragmentary perspective view of the preferred embodiment of the apparatus of the present invention illustrating a camming of the blade away from the handle;

FIG. 12 is a perspective fragmentary view illustrating a separation of the handle from the blade;

DETAILED DESCRIPTION OF THE PREFERRED EMBODIMENT

Figure 5:
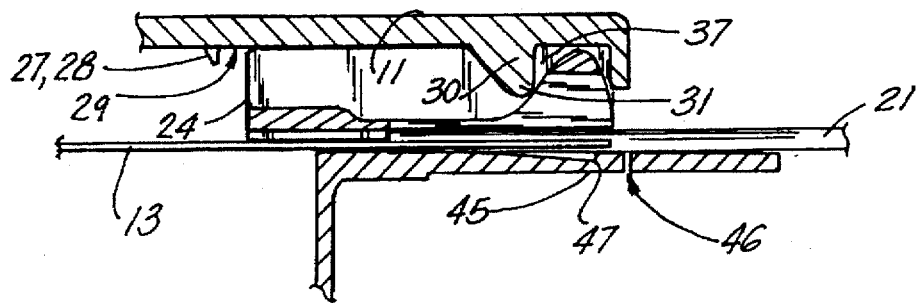
FIGS. 5–8 are sequential sectional views illustrating a removal of a surgical scalpel blade from a surgical scalpel handle according to the method and apparatus of the present invention.

FIGS. 1–4 and 13–18 show generally the preferred embodiment of the apparatus of the present invention that is designated generally in FIGS. 1–3 by the numeral 10. In FIGS. 1–3, scalpel blade removal apparatus 10 has housing 11 with a hollow interior 12 that can contain a large number of scalpel blades 13 that have been removed. The housing 11 can include a pair of separable sections including small housing section 14 and large housing section 15.

The housing sections 14 and 15 can be held together with assembly screws for example. In this fashion, the housing 11 could be opened to dispose of blades 13 contained inside. However, apparatus 10 is preferably disposable, being discarded when filled with blades 13. Corresponding edge portions 16, 17 align and engage upon assembly of the sections 14, 15 as shown in FIGS. 1 and 2.

The housing 11 has a receptacle 18 with a passageway 19 that receives the distal or lower end of blade 13 of scalpel 20. In FIG. 4, scalpel 20 includes a handle 21, tang 22, and removable blade 13.

In FIG. 1A, the handle 21 includes a shoulder 21A that receives blade 13 proximal end 13A. Handle 21 has a narrowing section 21B that connects integrally with the upper end 22A of tang 22. Tang 22 has a lower end 22D, a peripheral slot 22C and a rib 22B above slot 22C. The blade 13 has a longitudinal slot 13B with a narrowed section 13C that fits slot 22C of tang 22. Blade 13 cutting edge 13D is also shown in FIG. 1A.

As shown by the arrow 23 in FIG. 4, the user moves scalpel 20 along a linear path designated by the letter "A" in FIG. 4 when it is desired to remove a blade 13 from handle 21. The letter "A" in FIG. 4 also defines a plane that is co-planar with the plane of blade 13 in FIG. 4.

With the present invention, the user is not required during removal to twist or bend the handle 20 after the blade 13 is inserted into the housing 11 at receptacle 18. Rather, the user simply pushes the scalpel 20 in the direction of arrow 23 and along the line "A" into passageway 19.

Once the blade 13 and tang 22 are fully engaged into passageway 19, a stop is provided to prevent further inward movement of the scalpel 20. The user then recognizes that the scalpel 20 has traveled as far as it is going to travel. Once this "stop" is sensed by the user, the user withdraws the handle 20 and the blade 13 remains with the interior 12 of the housing 11.

FIGS. 5–18 show more clearly the construction of housing 11 and the working parts of receptacle 18 that are used to remove each blade 13 from handle 20. In FIGS. 5–18, a moving cam member 24 is provided that travels between a pair of sidewalls 25, 26 of small housing section 14. A pair of stops 27, 28 define the lower limit of travel of moving cam member 24. A rectangular surface 29 is wear surface that is engaged by a rectangular bearing surface 39 of moving cam member 24. Raised portion 30 has a pair of spaces 32, 33 on its sides thus providing a space for placement of the flanges 34, 35 of moving cam member 24.

During use, the user inserts scalpel 20 into passageway 19. The tang 22 travels into slot 36 until the lower tip of the tang 22 engages stop 42 (see FIGS. 5 and 10). Continued pressure in the direction in the direction of arrows 23 causes the entire camming member 24 to move downwardly. This pressure applied to handle 21 by the user pushes the moving cam member 24 in the direction of arrows 52 in FIG. 6. Ramp 37 of camming member 24 engages cam surface 31 of raised portion 30. At the same time, the camming member 24 rotates away from raised portion 30 as shown by arrow 53 in FIG. 6.

Figure 6:
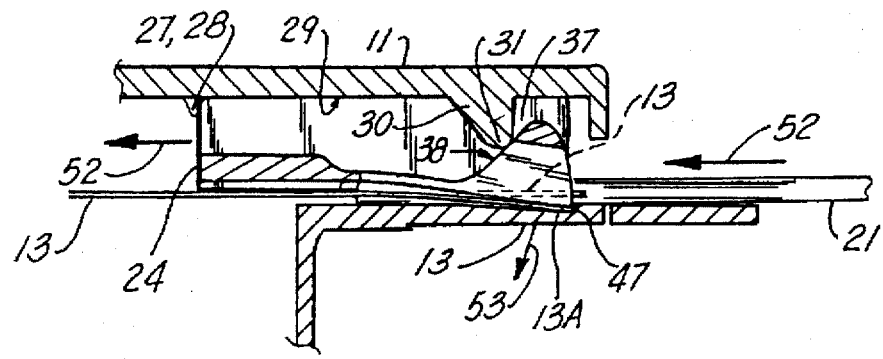

The rotation of the moving cam member 24 causes its flat surfaces 43, 44 to engage the proximal end 13A of blade 13, disengaging proximal end 13A of blade 13 from tang 22 (FIGS. 6 and 11). The angled surface 38 of cam moving member hits camming surface 31 and rotates the camming member 24 away from rectangular surface 29. The bearing surface 39 of moving cam member 24 remains in contact with rectangular surface 29 until cam moving member 24 reaches stops 27 and 28.

Because the proximal end of cam moving member 24 rotates away from surface 29, a spring arm 45 is provided on housing 11 that can flex so that the blade proximal end 13A can in fact rotate away from tang 22. Spring arm 45 is surrounded by slot 46 on three sides so that spring arm 45 can bend when pressure is applied thereto by the proximal end 13A of blade 13 and the proximal end of moving cam member 24. In FIGS. 6–7, 12, and 13, a catch 47 provides an edge 51 that engages the extreme proximal end of blade 13. The moving cam member 24 is maintained in alignment because its flanged portions 34, 35 are contained within sidewalls 48, 49 and 25, 26.

In FIGS. 5–8, the sequence of removal of blade 13 from handle 21 is illustrated. In FIG. 5, the blade 13 and handle 21 has been placed fully into passageway 19. The tang 22 has engaged moving cam member 24 and occupies slot 36 portion thereof. The extreme distal end of tang 22 is positioned at stop 42. In FIG. 5, the user has not pushed the moving cam member 24 to its lowermost position wherein it engages stops 27, 28.

Figure 7:
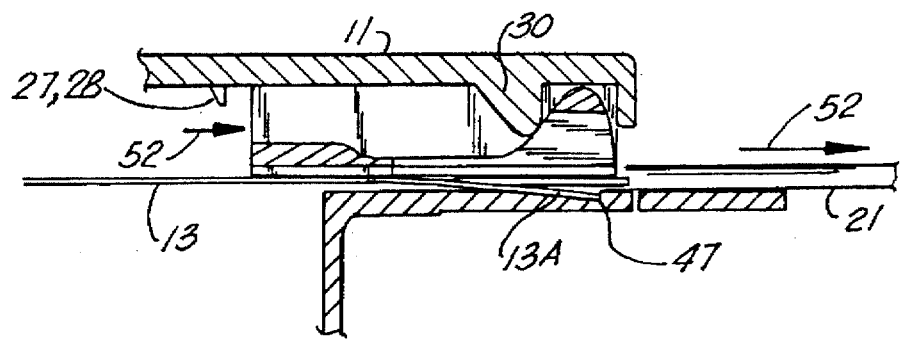
Figure 8:
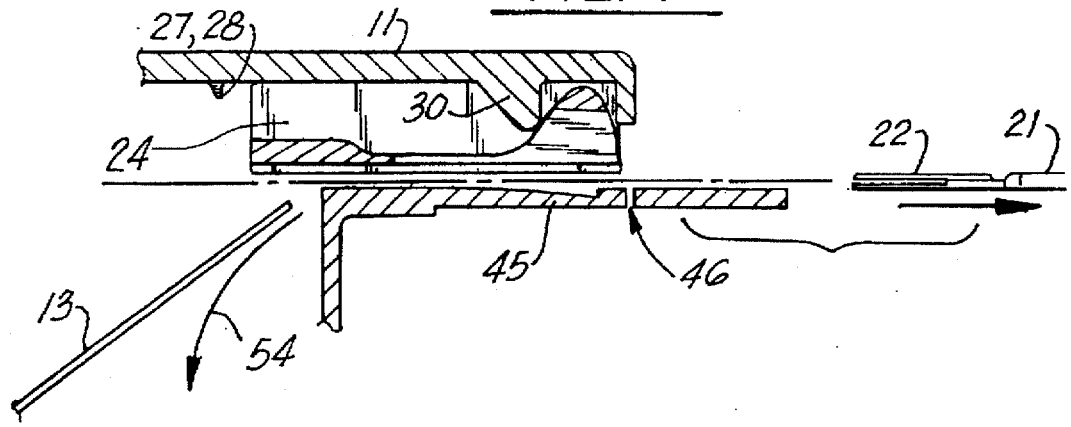
Figure 13:
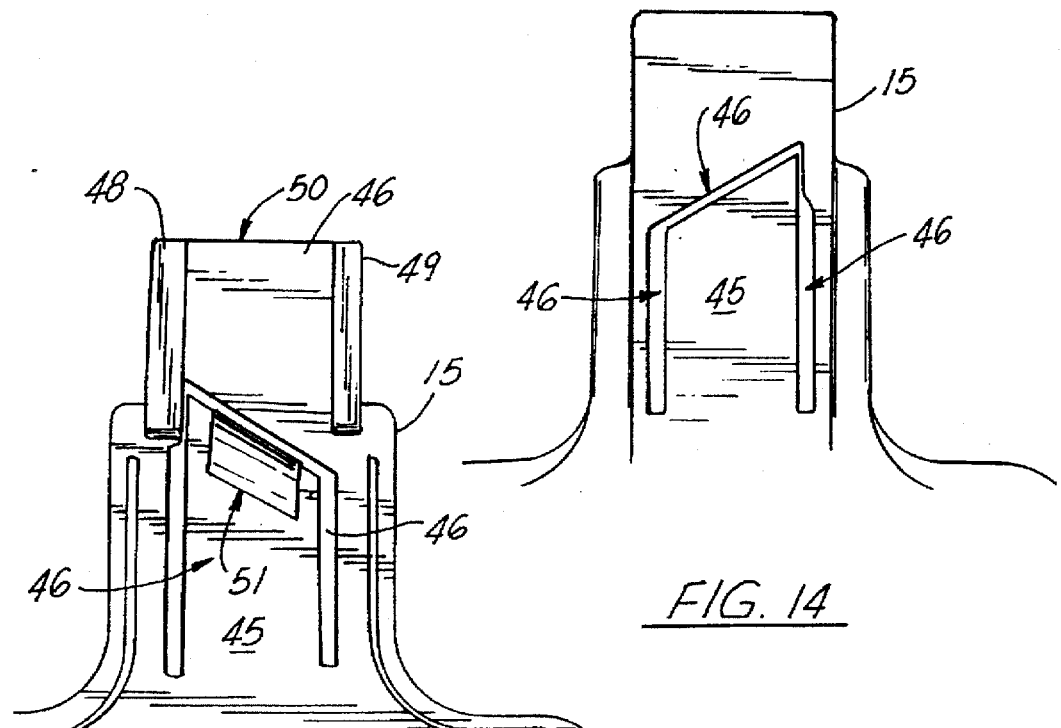
FIG. 13 is a partial fragmentary view of the housing portion of the preferred embodiment of the apparatus of the present invention.
Figure 14:
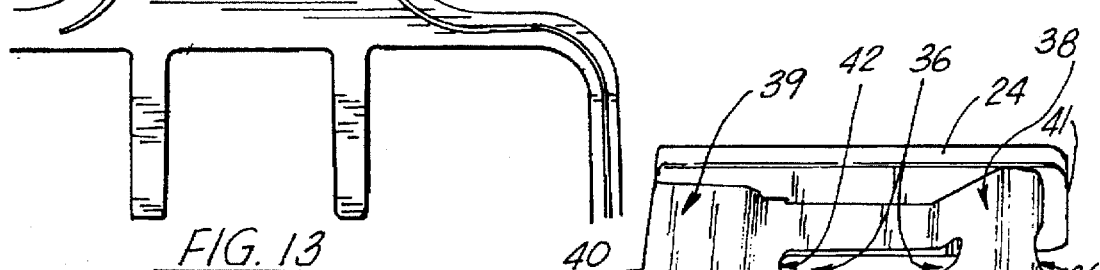
FIG. 14 is another fragmentary elevational view of the housing portion of the preferred embodiment of the apparatus of the present invention.
Figure 15:
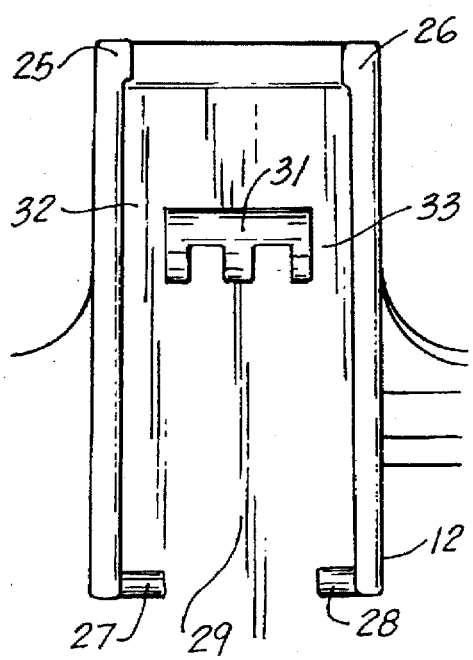
FIG. 15 is a fragmentary view of the housing portion of the preferred embodiment of the apparatus of the present invention illustrating the cam surface portion thereof.
Figure 16:
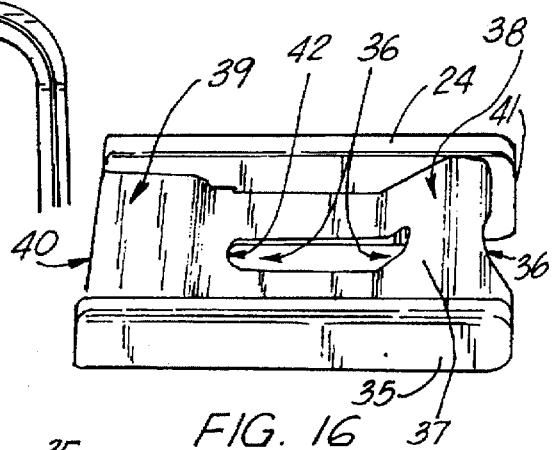
FIG. 16 is a perspective fragmentary view of the preferred embodiment of the apparatus of the present invention illustrating the moving cam member.
Figure 17:
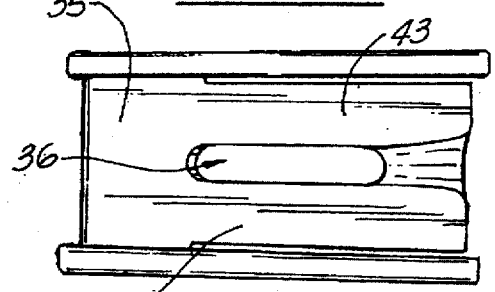
FIG. 17 is another perspective fragmentary view of the preferred embodiment of the apparatus of the present invention illustrating another view of the moving cam member.
Figure 18:
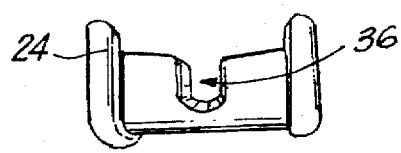
FIG. 18 is an end view of the cam member of FIGS. 16 and 17.

In FIG. 6, the moving cam member 24 has been pushed to its lowest position engaging the stops 27, 28. This causes the camming surface 38 of moving cam member 24 to rotate in the direction of arrow 53 as shown in FIG. 6. The flat surfaces 43, 44 of moving cam member 24 have bent proximal end 13A of blade 13 in the direction of arrow 53 thus disengaging the proximal 13A end of blade 13 from tang 22. This action engages the extreme proximal end 13A of blade 13 with shoulder 51 of catch 47. In FIG. 7, the user pulls on the handle 21 in the direction of arrow 54 removing handle 21. In FIGS. 6–7 and 11–12, the tang 22 is misaligned with the proximal 13A end portion of blade 13. Because the blade 13 is engaged under the shoulder 51 of catch 47, the blade 13 cannot leave with handle 21. Blade 13 is retained by the shoulder 51 as the handle 21 is removed as shown in FIG. 8.

Continued removal of the handle 21 and tang 22 from the slot 36 and stop 42 allows cam moving member 24 to travel away from stops 27, 28 in the direction of arrow 52 as shown in FIG. 7. As the moving cam member 24 returns to its original position, the blade 23 falls into the interior 12 of housing 11 (see arrow 54, FIG. 8). Once handle 21 is removed, spring arm 45 pushes the proximal end of moving cam member 24 back into its original position causing camming surface 38 to engage projecting portion 30. The combination of the removal of the tang 22 and the spring action of arm 45 returns the cam moving member 24 to the position of FIG. 8, ready to accept the next blade 13.

The following table lists the parts numbers and parts descriptions as used herein and in the drawings attached hereto.

PARTS LIST

| Part Number | Description |
|---|---|
| 10 | scalpel blade remover |
| 11 | housing |

-continued

PARTS LIST

| Part Number | Description |
|---|---|
| 12 | interior |
| 13 | scalpel blade |
| 13A | blade proximal |
| 13B | longitudinal slot |
| 13C | narrowed section |
| 13D | cutting edge |
| 14 | small housing section |
| 15 | large housing section |
| 16 | edge |
| 17 | edge |
| 18 | receptacle |
| 19 | passageway |
| 20 | scalpel |
| 21 | handle |
| 22 | tang |
| 22A | upper end |
| 22B | rib |
| 22C | peripheral slot |
| 22D | lower end |
| 23 | arrow |
| 24 | moving cam member |
| 25 | sidewall |
| 26 | sidewall |
| 27 | stop |
| 28 | stop |
| 29 | rectangular surface |
| 30 | raised portion |
| 31 | cam surface |
| 32 | space |
| 33 | space |
| 34 | rectangular flange |
| 35 | rectangular flange |
| 36 | longitudinal slot |
| 37 | ramp |
| 38 | angled surface |
| 39 | bearing surface |
| 40 | distal end |
| 41 | proximal end |
| 42 | stop |
| 43 | flat surface |
| 44 | flat surface |
| 45 | spring arm |
| 46 | space |
| 47 | catch |
| 48 | flange |
| 49 | flange |
| 50 | flat surface |
| 51 | shoulder |
| 52 | arrow |
| 53 | arrow |
| 54 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A scalpel blade removal apparatus for separating a changeable scalpel blade from a handle with a tang comprising:

a) a housing with an interior;

b) a receptacle on the housing with an opening for receiving the scalpel blade to be removed;

c) a moving cam member movably mounted in the receptacle between first and second positions;

d) a slot on the cam member that receives the tang of the handle;

e) a fixed cam surface on the housing that rotates the proximal end of the moving cam member as the moving cam member travels from the first to the second position;

f) spring means for urging the moving cam member from the second to the first position; and g) a catch that retains the blade within the housing when the moving arm member is in the second position and the tang withdrawn from the receptacle.

2. The apparatus of claim 1 wherein the moving cam member has proximal and distal end portions and the cam surface is on the proximal end portion.

3. The apparatus of claim 1 wherein the housing has an inside wall surface and the fixed cam surface projects from the inside wall surface.

4. The apparatus of claim 1 wherein the moving cam member has a pair of opposed generally parallel flange portions.

5. The apparatus of claim 1 wherein the receptacle includes a wear surface that engages the moving cam member during use.

6. The apparatus of claim 5 wherein the fixed cam surface is mounted on the wear surface.

7. The apparatus of claim 1 wherein the spring means is a spring arm mounted on the housing.

8. The apparatus of claim 1 wherein the receptacle has a socket that receives the blade along a linear path, a wear surface that tracks the linear path, and the moving cam member slides upon the wear surface.

9. The apparatus of claim 8 wherein the spring means is supported upon the housing at the receptacle, and the moving cam member is positioned in between the spring means and the wear surface.

10. A scalpel blade removal apparatus for separating a changeable scalpel blade from a handle with a tang comprising:

a) a housing with an interior;

b) a receptacle on the housing with an opening for receiving the scalpel blade to be removed;

c) a moving cam member movably mounted in the receptacle between first and second positions;

d) a slot on the cam member that receives the tang of the handle;

e) a fixed cam surface on the housing that rotates the proximal end of the moving cam member as the moving cam member travels from the first to the second position;

f) a spring arm on the housing for urging the moving cam member from the second to the first position;

g) a catch that retains the blade within the housing when the moving arm member is in the second position and the tang withdrawn from the receptacle; and h) wherein the moving cam member is positioned in between the fixed cam surface and the spring arm.

* * * * *